United States Patent [19]

Brothers et al.

[11] Patent Number: 4,673,647

[45] Date of Patent: Jun. 16, 1987

[54] PROCESS TO SOLUBILIZE ENZYMES AND AN ENZYME LIQUID PRODUCT PRODUCED THEREBY

[75] Inventors: Charles E. Brothers, Cassopolis, Mich.; Chong Y. Kim, Elkhart, Ind.

[73] Assignee: Miles Laboratories, Inc., Elkhart, Ind.

[21] Appl. No.: 730,864

[22] Filed: May 6, 1985

[51] Int. Cl.$^4$ .......................... C12N 9/02; C12N 9/00; C12N 9/20; C12N 9/28; C12N 9/34; C12N 9/50; C12N 9/56

[52] U.S. Cl. .................................. 435/189; 435/183; 435/198; 435/202; 435/205; 435/219; 435/222; 435/816

[58] Field of Search ............... 435/183, 189, 198, 202, 435/205, 220–222, 816, 219

[56] References Cited

U.S. PATENT DOCUMENTS

| | | | |
|---|---|---|---|
| 3,717,550 | 2/1973 | Ziffer | 435/220 |
| 3,819,528 | 6/1974 | Berry | 252/153 |
| 4,318,818 | 3/1982 | Letton et al. | 252/174.12 |
| 4,519,934 | 5/1985 | Eilertsen et al. | 252/174.12 |

FOREIGN PATENT DOCUMENTS 749329 6/1966 Canada .

*Primary Examiner*—Lionel M. Shapiro
*Attorney, Agent, or Firm*—Edward P. Gray; Jennifer L. Skord

[57] ABSTRACT

This invention relates to a novel process for the recovery of enzymes obtained from enzyme-producing microorganisms, and to the liquid enzyme product recovered by this process. Typically, the enzyme-containing filtrate from a fermentation of an enzyme-secreting microorganism is concentrated and a precipitation agent such as a salt or an organic solvent is added to the concentrate, thereby forming a cake. Then, a polyol solvent is circulated through the cake to solubilize the enzyme or enzyme complex from the cake and provide a liquid enzyme product. Particularly effective is propylene glycol as the polyol solvent. The liquid enzyme product may be shipped as is or subjected to further treatment to remove the solvent and create an essentially solvent-free enzyme product. The process is especially effective for the recovery of alkaline protease or alpa amylase.

29 Claims, No Drawings

PROCESS TO SOLUBILIZE ENZYMES AND AN ENZYME LIQUID PRODUCT PRODUCED THEREBY

This invention relates to a novel process for the recovery of an enzyme liquid product. The enzymes contemplated are those provided by enzyme-producing microorganisms, whether intracellular or extracellular. More particularly, the invention contemplates solubilizing or dissolving a precipitated enzyme or enzyme complex in a polyol solvent. The invention is particularly effective for the recovery of alkaline protease or alpha amylase in a liquid product form.

BACKGROUND OF THE INVENTION

Enzymes behave as biocatalysts, regulating many of the chemical reactions that naturally occur in living organisms. When isolated, enzymes also have many industrial, as well as medical uses. For instance, enzymes are used in the tanning industry and the detergent industry. Moreover, enzymes have many uses in the food industry, such as in the manufacture of cheese and alcoholic beverages.

In general, the traditional method in the production of enzymes has been to dissolve the enzyme in a water solution. Water, however, evaporates easily. Some enzymes, especially alkaline protease, are known to be potential health hazards to workers, and accordingly, it is desirable to keep them solubilized, i.e., prevent drying and/or dust formation. Dust and aerosols containing such enzymes can produce bronchial allergic reactions in sensitized persons. See, Flindt, "Pulmonary Disease Due to Inhalation of Derivatives of Bacillus Subtilis Containing Proteolytic Enzyme", *The Lancet*, from the Department of Occupational Health, University of Manchester, pages 1177-1184, (June 14, 1969). Moreover, enzymes such as alkaline protease (AP) easily precipitate out of a water solution. Thus, industrial production of such enzymes has been difficult due to their crystallization during the concentration steps employed in the traditional methods of production. These problems produced erratic yields and processing delays.

Thus, researchers had sought methods to keep enzymes, especially those that produce allergic reactions, dissolved in a closed system during processing. Nothing in the prior art, however teaches or suggests the use of a solvent other than water (or water with minor additives) to solubilize precipitated enzymes.

The prior art discloses that organic solvents, such as propylene glycol (PG), ethylene glycol (EG), and polyethylene glycol (PEG), may be employed during enzyme preparation. For instance, U.S. Pat. No. 4,497,897 discloses extraction of proteinase from Subtilisin Carlsberg using a solution of PG doped with carboxylate salt and calcium salt. U.S. Pat. No. 3,242,056 discloses a process employing aliphatic polyols in the preparation of lysozyme to promote heat stability in the lysozyme final product. U.S. Pat. No. 3,147,196 discloses a process in which tannin is added to an acidic enzyme-containing solution, and then the tannin-precipitated enzyme is extracted with an aqueous solution, which may contain PG or EG. However, tannin also ends up in the aqueous extract which is undesirable since tannin negatively interferes with the end use of the enzyme. Thus, additional processing is required so that the result is a solid, enzyme final product that is tannin-free. Also, U.S. Pat. No. 3,440,143 discloses extracting enzymes from plant tissue with an aqueous solution containing 0.5–5% of a high molecular weight PEG having at least 25 ethylene units to precipitate the phenols naturally present in plant tissue. None of the literature, however, suggests or discloses the present novel discovery of employing a novel solvent to prepare a solution of the enzyme.

SUMMARY OF THE INVENTION

The present invention provides for a process for the recovery of an enzyme product wherein the enzyme is provided by an enzyme-containing solution obtained from an enzyme-producing microorganism, said process comprising (a) adding a precipitation agent to the enzyme-containing solution to form a cake containing an enzyme or enzyme complex which is essentially insoluble in the solution and precipitates therefrom, (b) separating the cake containing the enzyme or enzyme complex from the solution, and (c) contacting the cake with a polyol solvent to solubilize the enzyme or enzyme complex from the cake to provide a polyol solution of the enzyme or enzyme complex, whereby a liquid enzyme product is recovered. Step (a) may be optionally preceded by concentrating the enzyme-containing solution, such as by evaporation or ultrafiltration. Also, step (c), may be optionally preceded by removing excess mother liquor to provide a relatively drier cake containing the enzyme or enzyme complex.

OBJECT AND ADVANTAGES

Accordingly, it is an object of the present invention to prepare commercially acceptable enzymes in a safer manner with good yield and satisfactory purity. The invention affords several advantages. Not only do workers like the ease of handling a liquid product as opposed to the difficulty of handling dry enzyme solids, but also they like avoiding inhaling enzyme dust. For instance, since polyols are hygroscopic and have a low vapor pressure, they do not evaporate as easily as water. Thus, a spill of a polyol solution of enzyme will not so readily produce enzyme dust if allowed to dry unnoticed as a water solution of enzyme would.

Furthermore, an ancillary advantage of the present invention is that polyols also have characteristics known to contribute to enhanced heat stability such as is disclosed in U.S. Pat. No. 3,242,056 mentioned above.

Moreover, because undesired, inadvertent enzyme crystallization has been avoided, this new method has significant economic advantages, which can be seen from the Chart below. This Chart is intended for illustrative purposes only and is not to be construed as required for teaching how to practice the present invention.

CHART

RECOVERY PROCESS FOR ALKALINE PROTEASE LIQUID PRODUCT

Comparison of Present Invention (1,2,3,4,5,6,7,8) with Traditional Method (1,2,3,4,5A,6A,7A)

| | | | |
|---|---|---|---|
| | | 1. Fermentor | |
| | | 2. Drop tank | |
| | | 3. Drum filter | |
| | | 4. Ultrafiltration | |
| 5A. | Evaporation: slow; high energy costs; enzyme crystallization probable | 5. | Na₂SO₄ precipitation of AP-containing cake |
| | | 6. | Separating cake with plate frame filter* |
| 6A. | Polishing: slow; possible loss of solid AP | 7. | Extraction by recycling PG** through AP-containing cake |

CHART-continued
RECOVERY PROCESS FOR ALKALINE PROTEASE LIQUID PRODUCT
Comparison of Present Invention (1,2,3,4,5,6,7,8) with Traditional Method (1,2,3,4,5A,6A,7A)

| | | | |
|---|---|---|---|
| 7A. | Formulation: relatively crude AP preparation since impurities have been concentrated with AP | 8. | collected on the plate frame filter<br>Formulation of PG extract*** |

*many impurities discarded in filtrate
**continuously ≧ 5 recycles; volume of PG is about 1/10 of volume prior to precipitation in No. 5 above
***substantially purer enzyme product at higher yield of AP The Chart illustrates an embodiment of the present invention, wherein the enzyme alkaline protease (AP) is extracted with propylene glycol (PG), as compared to the traditional method of enzyme preparation. A culture of an enzyme-secreting microorganism is grown in a fermentor (Step 1). Then, the fermentation products are moved from the fermentor into the drop tank (Step 2). A flocculant may be added in the drop tank to aid in removing solids thereby producing an enzyme-containing solution that is run through a drum filter (Step 3). The enzyme-containing solution then may be concentrated, usually by a factor of 2 using ultrafiltration (Step 4). Next, $Na_2SO_4$ is added to precipitate a cake containing the enzyme (Step 5) and liquor is removed from the cake with a plate frame filter (Step 6). The liquor carries with it many impurities, such as colorants, odors, et cetera. In the present invention the enzyme is handled in a liquid phase, i.e., it is dissolved in a polyol solvent which is PG in this Diagram (Step 7). Thus, the present invention avoids the possibility of undesired crystal formation as in the traditional method (Step 6A). Accordingly, worker exposure is minimized since the enzyme is in an enclosed system (Step 7) essentially until final recovery. Depending on desired end use, the liquid PG extract of AP may be marketed as is, or formulated (Step 8), which typically involves dilution with a compatible solvent such as water. Thus, from the Chart, it can be seen that the equipment, manpower and energy intensive steps of the traditional method are avoided by the present method. A substantially purer enzyme product results. It is now possible to obtain a liquid AP product with consistency and in good yield, which was not possible with traditional processing.

DETAILED DESCRIPTION OF THE INVENTION

In general, the present invention will work with any enzyme provided by an enzyme-containing solution obtained from an enzyme-producing microorganism. The enzyme may be intracellular or extracellular. A solution of an intracellular enzyme may be obtained by any of various, known methods to rupture the cell membrane, such as using detergents, sonication, milling, grinding, osmotic pressure, lysis, and the like, to release the intracellular enzyme from the cells, followed by removal of the cell debris.

Preferably, the enzyme is an extracellular enzyme provided by an enzyme-containing solution produced by the fermentation in a nutrient growth medium of enzyme-secreting microorganisms, such as bacteria, yeast, or fungi, followed by removal of the nutrient growth medium. The invention works especially well with enzymes selected from proteases, amylases, amyloglucosidases, lipases, and oxidases. In the preferred embodiment, the fermentation product, alkaline protease, is employed, which is useful in several industries, particularly the detergent industry.

After the microorganism produces the enzyme, typical processing involves conventional methods, such as filtration or centrifugation, to separate the solids and/or cell debris from the solution containing the enzyme. It is not necessary but it is preferred at this point that this solution containing the enzyme is then concentrated by at least a factor of 2 by means such as ultrafiltration or evaporation.

Next, a precipitation agent, such as a salt or a low molecular weight organic solvent is added to the enzyme-containing solution, or in the preferred embodiment where there has been concentration, then to the concentrated solution. Addition of the precipitation agent causes the enzyme and/or enzyme complex to precipitate, and a "slurry" or "cake" is produced. Throughout the description and claims, the term "cake" may be used interchangeably with the term "slurry", and it is intended to include those instances where the "cake" is so wet that it would be considered a "slurry". The cake containing the enzyme or enzyme complex is then separated from the remaining solution. Usually this separation is achieved by filtration and the filtrate containing impurities may be considered waste. If there is still excess mother liquor in the cake, it can be substantially removed from the slurry or cake by employing any of several methods. For instance, the excess mother liquor may be removed by additional regular filtration or by a pressure differential (such as suction filtration), gravity sedimentation, or centrifugation. The removal may be followed by a water wash and air blowing, providing a relatively drier cake.

The precipitation agents employed in the present invention are innocuous. By the term "innocuous" it is intended to mean that the precipitation agents contemplated by this invention (1) do not destroy the enzyme of interest, (2) do not negatively influence the end use of the enzyme product, and (3) do not require extensive additional processing to remove. It is unnecessary that the enzyme product be free of the precipitation agent. Thus, the precipitation agents contemplated by the present invention are other than those such as tannin, disclosed in the abovementioned U.S. Pat. No. 3,147,196. The presence of tannin in the enzyme product is very undesirable because tannin interferes with the availability of active enzyme sites. The precipitation agents contemplated by the present invention are broadly useful for many enzymes.

It is preferred to employ a salt as the precipitation agent in the present invention, but low molecular weight organic solvents will work well too as long as they are compatible with the particular polyol employed for solubilizing the enzyme. Preferred organic solvent precipitation agents are methyl ethyl ketone, acetone, methanol, ethanol, 1-propanol, isopropanol, tert-butanol, n-butanol, dimethyl formamide, dimethyl sulfoxide, monoethyl ether of ethylene glycol, monomethyl ether of ethyl glycol, and the like.

Organic solvent precipitation agents may be added to the solution containing the enzyme in a volume amount of 2 to 3 times the volume of the enzyme-containing solution. In a preferred embodiment with ethanol as the precipitation agent, the enzyme-containing solution is first concentrated by a factor of two and the volume of ethanol is 2.5 times the volume of the concentrated enzyme-containing solution.

If a salt is used as the precipitation agent, it should be selected from the Group I metal salts, the Group II metal salts, the corresponding ammonium salts of the Group I or II metal salts, or mixtures thereof. It is preferred that the valency of the anion of the salt be divalent or higher. Preferred are the phosphate, sulfate, and citrate salts. The especially preferred salts are sodium phosphate, ammonium phosphate, sodium citrate, sodium sulfate and ammonium sulfate. Potassium and cessium salts may also be employed, but of course these are more expensive. Sulfate salts are most desirable. Salt precipitation agents may simply be added to the solution containing the enzyme, in the amount of 5–50% weight/volume of salt agent to enzyme-containing solution. More preferably, the salt agent is added in the amount of 12–25% weight/volume. Also, the salt agent may be dissolved in water and the aqueous solution added.

Next, a polyol solvent, which is PG in the preferred embodiment, is circulated through the cake in order to solubilize and recover the enzyme and/or enzyme complex from the cake. It is intended here that the term "to solubilize" means the same thing as the term "to dissolve" or "to extract" and the terms may be used interchangeably. Also, the term "polyol solvent" as used here is intended to mean 100% polyol, essentially 100% polyol, or a polyol-containing solution wherein the polyol is in combination with a compatible co-solvent.

The polyols contemplated in this invention comprise low molecular weight polyethylene glycol and the $C_2$ through $C_8$ alcohols having at least two OH groups. $C_2$–$C_8$ alcohols with more than two OH groups, such as glycerol, may be employed, but it is preferred that there be present only two OH groups. It is especially desirable that these two OH groups be present on adjacent carbon atoms in the chain, and that the $C_2$–$C_8$ alcohol be aliphatic and have a straight carbon chain. Suitable polyols include, for example, ethylene glycol, propylene glycol, glycerol, the low molecular weight (about 900 or less) polyethylene glycols, and mixtures thereof.

The polyol may be in solution with a co-solvent for the enzyme, said co-solvent being compatible with the polyol. The co-solvent of course may be water but also may be selected from organic solvents such as acetone, methyl ethyl ketone, methanol, ethanol, 1-propanol, isopropanol, tert-butanol, dimethyl formamide, dimethyl sulfoxide, monomethyl ether of ethylene glycol, monoethyl ether of ethylene glycol, and the like. If the polyol is used in solution with a co-solvent, it is preferred that the polyol be present in an amount of at least 20% by volume, and more preferably 50%. Higher concentrations of polyol, up to 100% polyol with no co-solvent, may also be advantageously employed. Also, the amount of co-solvent may depend on the co-solvent used. For instance, ethanol may also be used as a precipitation agent, i.e. in step (a) of the Summary of Invention mentioned supra. Thus, too much ethanol as a co-solvent with the polyol may cause precipitation rather than solubilization of the enzyme.

The polyol solvent may be circulated through the enzyme-containing cake once, but preferably it is recirculated through the cake at least twice to enhance extraction of the enzyme. It is particularly desirable to employ at least 5 recirculations, and up to as many as 100, or more recirculations may be advantageously employed. The result is a liquid enzyme product, which is a polyol solution of the enzyme or enzyme complex. If a salt precipitation agent has been used, the resultant polyol solution of the enzyme or enzyme complex may be cooled to a temperature in a range between room temperature and the freezing point of this solution to cause excess salt to precipitate. In a preferred embodiment with alkaline protease, the cooling is down to approximately 16° C.

Depending on the desired end use, the polyol solution of the enzyme or enzyme complex may be used as is, as a liquid enzyme product, or the solvent may be substantially removed so that the enzyme by itself may be used. Removal of the solvent may be achieved by one or more known techniques or combinations thereof, thereby providing a substantially solvent-free enzyme product. One such technique is ultrafiltration, and another is reprecipitation of the enzyme followed by filtration and/or centrifugation to remove liquid.

The present invention also contemplates re-slurrying of the cake in the polyol solvent, but more safety features result from recirculating the polyol solvent through the cake. Recirculation typically occurs in a closed system, i.e. the polyol solvent may be flowing through a pipe. On the other hand, when a cake is re-slurried, it is exposed to air and could become too dry, thereby subjecting the worker handling it to inhalation of enzyme dust. Nevertheless, an advantage of the present invention is that even if the closed system becomes exposed to the air, the chance of the cake drying unnoticed and producing dust is minimal since polyols are hygroscopic.

Depending on the enzyme, adjusting the pH toward the acid range during recirculation or reslurrying may enhance extraction. A minor amount of an acid such as acetic, sulfuric or hydrochloric may be advantageously employed for pH adjustment.

Any polyol extract may be formulated, if desired. A preferred method involves extraction with propylene glycol as the polyol solvent and then formulating the PG extract by diluting it with a co-solvent such as diluting it with water to 30% volume PG extract and 70% volume $H_2O$. Any of the other co-solvents mentioned above may also be employed in formulating the extract. The reason for formulating is to cut the enzyme activity down to whatever is desired depending on the end use of the liquid enzyme product. Care must be taken not to use too much co-solvent during the formulation or the enzyme may precipitate instead of remaining in solution.

In another preferred embodiment, the volume of the enzyme-containing solution or concentrated solution immediately before the step of adding the precipitation agent as compared to the volume of the polyol solvent that is circulated through the cake is in a ratio of approximately 30:1 to 2:1, and more preferably 10:1.

The following examples illustrate the preferred embodiments of the present invention, and are not intended to limit the claims to the embodiments disclosed in the examples. The examples illustrate preferred embodiments employing alkaline protease and alpha-amylase both of which are fermentation products of *Bacillus licheniformis*.

Fermentation of *Bacillus licheniformis* to Produce Alkaline Protease

Media suitable for the fermentation of alkaline protease for a 1000 liter fermentor are as follows:

| | |
|---|---|
| Soy Media | 50-100 kg |
| Sodium Citrate | 4-5 kg |
| Calcium Chloride Dihydrate | 4-5 kg |
| A Starch | 50-200 kg |
| Antifoam | 235-280 ml |
| α-amylase (TAKA-THERM ® L-170)[1] | 40-55 gm |
| Mono- and Disodium phosphate | 14-17 kg |
| Water added to | 1000 L total volume |

[1]TAKA-THERM ® is a trademark of Miles Laboratories, Elkhart, Indiana, for a broad class of carbohydrase enzymes. The particular TAKA-THERM used here is α-amylase.

The media was inoculated with viable cells of *Bacillus licheniformis* and allowed to ferment for 30 to 48 hours 35°-40° C. After this fermentation, the broth was diluted with $H_2O$ by 50% of the initial drop volume and flocculated by a suitable flocculant to aid in biomass removal. The flocculated biomass was removed by centrifugation and the liquid passed through a precoated vacuum drum filter to provide a cell-free filtrate. The Detergent Alkaline Protease Units per milliliter (DAPU/ml) was determined by the Manual of Detergent Alkaline Protease Assay, and was between 60 and 70 DAPU/ml.

Fermentation of *Bacillus licheniformis* to Produce Alpha-Amylase

Media suitable for the fermentation of alpha-amylase for a 1000 liter fermentor are as follows:

| Fermentation of *Bacillus licheniformis* to Produce Alpha-Amylase | |
|---|---|
| Media suitable for the fermentation of alpha-amylase for a 1000 liter fermentor are as follows: | |
| Sodium Citrate | 0-5 kg |
| Calcium Chloride Dihydrate | 0.2-1.0 kg |
| Mono-and Dipotassium Phosphate | 15-24 kg |
| Ammonium Sulfate | 2-7 kg |
| A Sugar | 100-200 kg |
| Cotton Seed Meal | 25-40 kg |
| Soy Media | 30-50 kg |
| Antifoam | 8-13 L |
| Water added to | 1,000 L total volume |

The media was inoculated with viable cells of *Bacillus licheniformis* and allowed to ferment for 70-90 hours at 40°-45° C. while maintaining the pH at approximately neutral. After this fermentation, the media was flocculated by a suitable flocculant to aid in biomass removal. The biomass was removed by centrifugation and the liquid passed through a drum filter to provide a cell-free filtrate. The Modified Wohlgemuth Units per milliliter (MWU/ml) was determined by the Manual Liquefying Alpha-Amylase Assay which is a modification of the method disclosed by Wohlgemuth in *Biochem.* 29:1 (1908), and was between 100,000 and 120,000 MWU/ml.

EXAMPLE I

The filtrate (enzyme-containing solution) from the 1000 liter alkaline protease fermentation was concentrated by ultrafiltration through PM-2 membranes down to about 500 liters of concentrate. The PM-2 membranes are polysulfone membranes supplied by Romicon Company. The shortened notation PM-2 is used to indicate the membrane is permeable by substances having a molecular weight of approximately 2000 or less. Sodium sulfate was then dissolved in the concentrate in the amount of 17% weight/volume, resulting in a slurry of enzyme precipitate. FW-6 Dicalite TM admix (an inert silaceous filter aid supplied by Eagle Pitcher Industries) was added to the slurry in the amount of 0.6% weight/volume of concentrate to enhance the rate of filtration. The slurried batch was filtered through a Sparkler TM apparatus. The Sparkler filter apparatus is supplied by Sparkler Manufacturing Company of Conroe, Tex. and some patents covering these filter apparatus are U.S. Pat. Nos. 2,460,423, 2,760,641, and 2,639,251. A Sparkler apparatus employs horizontally disposed paper-type filters. Pressure was applied to remove excess mother liquor and provide about 25 kg of filter cake containing the alkaline protease precipitate. Next, the cake was washed with a minimal amount of water and then blown with ambient air to displace the balance of the mother liquor. Next, 20 liters of propylene glycol were recirculated through the cake inside of the filter apparatus for 2.5 hours in order to dissolve the enzyme. During recirculation, the pH of the PG solution of alkaline protease was periodically adjusted with acetic acid to $6.2 \pm 0.2$. Afterward, cold water was then run through the filter apparatus jacket reducing the temperature of the propylene glycol solution of enzyme to approximately 16° C. The cooling caused precipitation of excess sodium sulfate, thereby removing this excess from the propylene glycol solution containing the enzyme. The result was an enzyme liquid product comprising a propylene glycol solution of alkaline protease. Recovery was calculated by assaying a small portion of the 500 liter concentrate and comparing that enzyme activity to the enzyme activity determined from assaying a small portion of the PG solution of the enzyme. Recovery of enzyme was 84%.

EXAMPLE II

The procedure of Example I was repeated, except that a plate-frame filter apparatus was employed instead of a Sparkler TM filter apparatus. A plate-frame filter apparatus employs vertically disposed cloth-type filters. No water wash was done in this apparatus. Recovery was calculated in the same manner as Example I and was 80%.

EXAMPLE III

The procedure of Example II was repeated, except that a filter-press apparatus was employed instead of a plate-frame filter apparatus, and after filtering the apparatus was cracked open enough to allow excess mother liquor to drain from the slurry, and then reclosed for extraction of the enzyme with PG. Recovery was calculated in the same manner as in Example I and was 74%.

EXAMPLE IV

The procedure of Example I was repeated, except that 22% weight/volume of ammonium sulfate was employed instead of the sodium sulfate. Recovery was calculated in the same manner as Example I and was 85%.

EXAMPLE V

The procedure of Example I was repeated except that the filtrate from the 1000 liter alpha-amylase fermentation was employed instead of the filtrate from the alkaline protease fermentation, and the amount of $Na_2SO_4$ was 22% weight/volume. Also, there was no pH adjustment with acetic acid. Recovery was calculated in the same manner as Example I and was 84%.

EXAMPLE VI

The procedure of Example II was repeated except that the filtrate from the 1000 liter alpha-amylase fermentation was used instead of the filtrate from the alkaline protease fermentation and 22% weight/volume $Na_2SO_4$ was used. Also, there was no pH adjustment with acetic acid. Recovery was calculated in the same manner as Example I and was 84%.

EXAMPLE VII

The procedure of Example III was repeated except that the filtrate from the 1000 liter alpha-amylase fermentation was used instead of the filtrate from the alkaline protease fermentation and the amount of $Na_2SO_4$ was 22% weight/volume. Also, there was no pH adjustment with acetic acid. Recovery was calculated in the same manner as Example I and was 84%.

EXAMPLES VIII–XV

The procedures of Examples I–VII, respectively, were repeated, except that instead of circulating the PG through the cake in the filter apparatus, the cake was removed from the filter apparatus and re-slurried in the PG. Recoveries were calculated in the same manner and were approximately 82% to 89%.

EXAMPLE XVI

The procedure of Example I was repeated, except that 1250 liters of ethanol were employed as the precipitation agent instead of the $Na_2SO_4$, resulting in a slurry of an enzyme precipitate. Thus, it was unnecessary to cool to remove excess $Na_2SO_4$. Also, the ethanol kept the extraction sufficiently acidic so that no pH adjustment with acid was necessary. Recovery was calculated in the same manner as in Example I and was 85%.

We claim:

1. A process for the recovery of an enzyme product wherein the enzyme is provided by an enzyme-containing solution obtained from an enzyme-producing microorganism, said process comprising;
   (a) adding an innocuous precipitation agent to the enzyme-containing solution to form a cake containing an enzyme or enzyme complex which is essentially insoluble in the solution and precipitates therefrom;
   (b) separating the cake containing the enzyme or enzyme complex from the solution; and,
   (c) contacting the cake with a polyol solvent to solubilize the enzyme or enzyme complex from the cake to provide a polyol solution of the enzyme or enzyme complex, whereby a liquid enzyme product is recovered.

2. The process of claim 1, wherein prior to step (a) there is further included concentrating the enzyme-containing solution by at least a factor of two.

3. The process of claim 2, wherein the separating in step (b) is achieved by filtration.

4. The process of claim 3, wherein after step (b) there is included step (b′) removing excess mother liquor and subjecting the cake to a water wash and air blowing to provide a relatively drier cake containing the enzyme or enzyme complex.

5. The process of claim 1, wherein the contacting with polyol solvent in step (c) is achieved by circulating a solution containing at least 20% by volume polyol in combination with a co-solvent for the enzyme at least once through the filter cake.

6. The process of claim 1, wherein the contacting with polyol solvent in step (c) is achieved by re-slurrying the cake with a solution containing at least 20% by volume polyol in combination with a co-solvent for the enzyme.

7. The process of claim 5 or 6, wherein the co-solvent is acetone, methyl ethyl ketone, methanol, ethanol, 1-propanol, isopropanol, t-butanol, n-butanol, dimethyl formamide, dimethyl sulfoxide, monoethyl ether of ethylene glycol, monomethyl ether of ethylene glycol, water, or a mixture thereof.

8. The process of claim 1, wherein the contacting with polyol solvent in step (c) is with essentially 100% polyol.

9. The process of claim 8, further including (d) formulating the polyol solution of the enzyme or enzyme complex by dilution with water or an organic solvent on a volume/volume basis in the range of 99–30% polyol solution of enzyme or enzyme complex and 1–70% water or organic solvent.

10. The process of claim 4, 5, 6, or 8, further including (d) treating the polyol solution of the enzyme or enzyme complex whereby there is provided a substantially solvent-free enzyme product.

11. The process of claim 10, wherein the further treatment includes ultrafiltration.

12. The process of claim 10, wherein the further treatment includes precipitating the crystal form of the enzyme, followed by filtration or centrifugation to remove liquid.

13. The process of claim 1, wherein the enzyme-producing microorganism is *Bacillus licheniformis*.

14. The process of claim 1, wherein the enzyme is selected from the group consisting of proteases, amylases, amyloglucosidases, lipases, and oxidases.

15. The process of claim 5, 6, or 8, wherein the polyol employed is a low molecular weight polyethylene glycol, a $C_2$–$C_8$ polyol, or a mixture thereof.

16. The process of claim 15, wherein the polyol is glycerol, ethylene glycol, propylene glycol, polyethylene glycols having a low molecular weight of about 900 or less, or a mixture thereof.

17. The process of claim 1, wherein the precipitation agent is a salt or a low molecular weight organic solvent.

18. The process of claim 17, wherein the organic solvent is acetone, methyl ethyl ketone, methanol, ethanol, 1-propanol, isopropanol, t-butanol, n-butanol, dimethyl formamide, dimethyl sulfoxide, monoethyl ether of ethylene glycol, monomethyl ether of ethylene glycol, or a mixture thereof.

19. The process of claim 17, wherein the salt is selected from the group consisting of the Group I metal salts, the Group II metal salts, the corresponding ammonium salts of the Group I or II metal salts, and a mixture thereof.

20. The process of claim 19, wherein the valency of the anion of the salt is divalent or higher.

21. The process of claim 20, wherein the salt is sodium sulfate, ammonium sulfate, sodium phosphate, ammonium phosphate, sodium citrate, or a mixture thereof.

22. The process of claim 19, further including cooling the polyol solution of the enzyme or enzyme complex whereby excess salt is precipitated and thereby removed from the polyol solution.

23. The process of claim 22, wherein the enzyme is alkaline protease and the pH is adjusted to approximately 6.0 to 6.4 during contacting with polyol solvent.

24. The process of claim 1, wherein the ratio of the volume of enzyme-containing solution to the volume of polyol solvent is in the range of 30:1 to 2:1.

25. The process of claim 3, further including admixing a small amount of filter aid into the cake to aid in the filtration.

26. A process for the recovery of an enzyme product wherein the enzyme is provided by an enzyme-containing solution obtained from the fermentation of an enzyme-producing microorganism in an aqueous nutrient growth medium comprising:
 (a) filtering or centrifuging the nutrient growth medium to remove solids therefrom and provide a solution containing an enzyme;
 (b) concentrating to provide a concentrated solution;
 (c) adding an innocuous precipitation agent selected from the group consisting of salts and low molecular weight organic solvents to the concentrated solution to form a wet cake containing an enzyme or enzyme complex which is essentially insoluble in the concentrated solution and precipitates therefrom;
 (d) removing excess mother liquor from the wet cake to provide a relatively drier cake; and,
 (e) circulating a polyol solvent at least once through the cake to solubilize the enzyme or enzyme complex from the cake to provide a polyol solution of enzyme or enzyme complex, wherein the volume of the concentrated enzyme-containing solution in (b) and the volume of the polyol solvent are in a ratio in the range of 30:1 to 2:1.

27. The process of claim 26, wherein the precipitation agent is selected from salts and the process further includes:
 (e') cooling the polyol solution of enzyme or enzyme complex to below room temperature whereby excess salt is precipitated and thereby removed from the polyol solution.

28. The process of claim 27, wherein the salt is sodium sulfate, ammonium sulfate, sodium phosphate, ammonium phosphate, sodium citrate, or a mixture thereof, and the polyol solvent that is circulated is at least 20% by volume propyleneglycol.

29. The process of claim 28, further including:
 (f) treating the polyol solution of enzyme or enzyme complex to remove substantially all the solvent thereby yielding an essentially solvent-free enzyme product.

* * * * *